(12) United States Patent
Boit et al.

(10) Patent No.: US 8,940,393 B2
(45) Date of Patent: Jan. 27, 2015

(54) MANNITOL CRYSTAL POWDER HAVING A LOW FINE-PARTICLE CONTENT, AND METHOD FOR PRODUCING SAME

(75) Inventors: Baptiste Boit, Bethune (FR); Philippe Lefevre, Haverskerque (FR); Jose Lis, La Gorgue (FR)

(73) Assignee: Roquette Freres, Lestrem (FR)

( * ) Notice: Subject to any disclaimer, the term of this patent is extended or adjusted under 35 U.S.C. 154(b) by 245 days.

(21) Appl. No.: 13/393,570

(22) PCT Filed: Sep. 1, 2010

(86) PCT No.: PCT/FR2010/051822
§ 371 (c)(1),
(2), (4) Date: Mar. 1, 2012

(87) PCT Pub. No.: WO2011/027078
PCT Pub. Date: Mar. 10, 2011

(65) Prior Publication Data
US 2012/0156496 A1  Jun. 21, 2012

(30) Foreign Application Priority Data

Sep. 1, 2009  (FR) .................................. 09 55959

(51) Int. Cl.
| | |
|---|---|
| *B32B 5/16* | (2006.01) |
| *A61K 9/14* | (2006.01) |
| *C07C 29/78* | (2006.01) |
| *C07C 31/26* | (2006.01) |
| *A61K 9/20* | (2006.01) |
| *C07H 1/06* | (2006.01) |

(52) U.S. Cl.
CPC . *C07C 29/78* (2013.01); *C07H 1/06* (2013.01); *C07C 31/26* (2013.01); *A61K 9/2018* (2013.01)
USPC .............. 428/402; 424/489; 426/96; 426/443

(58) Field of Classification Search
USPC ...................... 428/402; 426/96, 443; 424/489
See application file for complete search history.

(56) References Cited

U.S. PATENT DOCUMENTS

| 1,861,248 | A | 5/1932 | Stebbins |
| 4,670,611 | A | 6/1987 | Lemay |
| 5,573,777 | A | 11/1996 | Serpelloni |
| 6,743,447 | B2 * | 6/2004 | Labergerie et al. ........... 424/489 |
| 2003/0026832 | A1 | 2/2003 | Labergerie et al. |

FOREIGN PATENT DOCUMENTS

| EP | 0 202 168 | 11/1986 |
| EP | 0 645 096 | 3/1995 |
| EP | 1 138 661 | 10/2001 |

OTHER PUBLICATIONS

Debord, Study of different crystalline forms of mannitol: comparative behavior under compressioin, Drug Development and Industrial Pharmacy, 13 (9-11), 1533-1546 (1987).*
International Search Report dated Nov. 18, 2010, corresponding to PCT/FR2010/051822.

* cited by examiner

*Primary Examiner* — Holly Le
(74) *Attorney, Agent, or Firm* — Young & Thompson

(57) ABSTRACT

Disclosed is a powder composition of mannitol crystals, produced by: (i) the crystallization of mannitol in a solvent; followed by (ii) a step of separating the crystals from the resulting crystal suspension; (iii) a step of drying the crystals; and (iv) a selection step, the composition having a particle size distribution, as determined by laser particle sizing, of 72 to 99.9 vol % of particles having a particle size greater than 75 µm, of 0.1 to 60 vol % of particles larger than 250 µm, and a mean diameter of between 100 and 300 µm. Also described is a method for producing such a composition by a step of crystallizing a mannitol syrup followed by drying the mannitol crystals, a step of selecting particles, and a step of collecting a fraction of the powder composition including 72 to 99.9% of particles having a particle size greater than 75 µm.

20 Claims, No Drawings

MANNITOL CRYSTAL POWDER HAVING A LOW FINE-PARTICLE CONTENT, AND METHOD FOR PRODUCING SAME

The present invention relates to a pulverulent composition formed of mannitol crystals which is depleted in fine particles. The invention also relates to the process for producing such a pulverulent mannitol composition.

1,2,3,4,5,6-Hexanehexol ($C_6H_{14}O_6$), commonly known as mannitol, is a polyol obtained by extraction from plants, such as algae, or by synthesis, such as by catalytic hydrogenation of mannose or fructose. The hydrogenation of mannose takes place with a stoichiometric yield and provides mannitol, whereas the catalytic hydrogenation of fructose, although making it possible to obtain mannitol, has a nonstoichiometric yield since the hydrogenation of fructose is not stereospecific and provides an equal amount of sorbitol.

Mannitol is of great interest because of its chemical stability, a virtually zero hygroscopicity, its low calorific value and its glycemic index, which is lower than that of sucrose, while advantageously exhibiting a high solubility and a sweet and refreshing taste in the mouth. Furthermore, mannitol has the distinguishing feature of not being cariogenic, which is advantageous in the pharmaceutical or food industry, in particular in the field of confectionary and more particularly chewing gums. It thus makes possible the manufacture of confectionary which is noncariogenic insofar as the other ingredients of the formulation do not introduce fermentable sugars.

The prior art describes the use of crystallized mannitol in processes for producing chewing gums, which generally comprise five steps (Formulation and Production of Chewing and Bubble Gum, edited by Douglas Fritz, Kennedy's Publications Ltd, London, UK). During the first step, the various compounds are mixed using a kneading machine comprising two Z-shaped blades. The complete cycle of the operation lasts from 15 to 20 minutes and the ingredients are added as the kneading proceeds in the kneading machine. In order to render the base gum malleable, the latter is heated beforehand and during mixing. At the end of kneading, the temperature of the paste is approximately 50° C. Two main groups are distinguished among the constituent ingredients of chewing gums, which groups are the components which are insoluble in water and thus in the saliva, such as mainly the base gum, and the components which are soluble in water, conferring on the chewing gum its flavor, such as sweeteners in particular. The mixing step is followed by a second step of extrusion under hot conditions, in order to obtain a strip of chewing gum which is narrower or wider according to the device used. In order to reduce the thickness of the strip obtained, a rolling step is provided. During this step, the strip passes successively between several pairs of rollers having a decreasing separation. The rolling step is followed by a final forming/cutting step, which can be a simple step of forming in combination with a cutting or preliminary cutting of the strip obtained before packaging. In point of fact, after the step of extrusion under hot conditions, the strip of gum is extremely sticky. In fact, in order to prevent it from being destroyed or losing its integrity during the rolling, a step of dusting over both faces of the strip is conventionally carried out between the extrusion and rolling steps. Numerous agents are used in the dusting powders. Thus, plasticizing agents or anticaking agents, such as talc, calcium carbonate, tricalcium phosphate, silica or silicates, are encountered. All these inorganic agents are capable of damaging the organoleptic properties of the chewing gums obtained. This is because these agents are insoluble and are devoid of flavor, indeed even are unpleasant, in the mouth.

Furthermore, the most widely used powder for the dusting is talc. In point of fact, talc may be the subject of contamination by a product having a very similar chemical nature but nevertheless very toxic: asbestos. Thus, the contaminated talc might be implicated in cancerization processes, whether cancer of the digestive tract, following absorption by the oral route, or cancer of the pulmonary tissue, during absorption by the respiratory route, in particular during the handling thereof. The handling of talc is thus regulated and respiratory protective equipment is obligatory for production personnel.

In order to reduce the amounts of talcs incorporated during the preparation of chewing gums, use is regularly made of powders formed of nonhygroscopic polyols, such as, in particular, mannitol. Generally, the polyol powders have a very fine particle size, in order to replace the talc, which itself has a very fine particle size (powder with a particle size of less than 40 μm and with a mean diameter of less than 10 μm), and in order not to be felt by the tongue during the tasting of the chewing gum.

However, complete replacement of the talc by these powders is not recommended since they have a very poor flow, rendering them unsuitable for dusting. In the case of partial replacement, the talc, which has a good flow, confers on the mixture a flow which is still mediocre but sufficient to allow the dusting of the strip of chewing gum. In point of fact, even in the context of a partial replacement of the talc, the reduction in flow of the powder mixture is such that it constricts the deposition of a large amount of powder on the strip of chewing gum, resulting in fact in significant waste, a deterioration in the quality of the chewing gums obtained or a modification to the conditions for regulating the devices.

Furthermore, the small particle size of these powders increases the generation of dust in suspension in the air, thus accentuating the risks to the handlers associated with the presence of asbestos in the talc.

Finally, a phenomenon is observed of solidification, in their packaging, of the powders formed of polyols having a fine particle size. This is because these powders are instable in that they cake on storage or during transportation. The bodies obtained can only be broken up by exerting very high forces.

Although the use of anticaking agents in the food industry results in regulatory restrictions, since they may be regarded as toxic or dangerous, this solution has been envisaged. However, while a reduction in caking has been demonstrated in the case of powders formed of hygroscopic polyols, no similar change in behavior is observed for powders formed of polyols which are not or only slightly hydroscopic. Consequently, these anticaking agents have an effect only on some powders and not on others, as is the case with mannitol.

The state of the art also provides, in order to improve the characteristics of pulverulent mannitol compositions, for additional atomization or granulation steps to be carried out after the crystallization of the mannitol. In point of fact, these processes prove to be relatively expensive.

In order to obtain a powder which is stable on storage and on transportation, having good flow characteristics, and particularly advantageous during the use thereof during processes for producing chewing gum, the invention relates to a pulverulent composition formed of mannitol crystals which is obtained by (i) crystallization of mannitol from a solvent, preferably from water, followed (ii) by a step of separation of the crystals from the suspension of crystals which is obtained, (iii) by a step of drying the crystals and (iv) by a step of selection, said composition exhibiting a particle size distribution by volume, determined by laser particle size analysis, exhibiting:

from 72 to 99.9%, preferably from 75 to 99%, more preferably from 80 to 98% and more preferably still from 85 to 97% of particles with a particle size of greater than 75 µm, from 0.1 to 60%, preferably from 1 to 55%, more preferably from 2 to 40% and more preferably still from 3 to 35% of particles of greater than 250 µm, a mean diameter of 100 to 300 µm, preferably of 120 to 270 µm, more preferably of 150 to 250 µm and more preferably still of 170 to 230 µm.

Within the meaning of the invention, "pulverulent composition formed of mannitol crystals" or "powder formed of mannitol crystals" is understood to mean the product obtained by crystallization of a pure or impure solution of mannitol, namely a solution comprising from 20 to 100% of mannitol with regard to dry matter. Mention will be made, for example, of European patent EP 0 202 168.

Such a process has the distinguishing feature of making it possible to obtain a composition formed of predominantly individual crystals. "Predominantly" is understood to mean more than 50% of individual crystals, preferably from 60 to 100%, indeed even from 70 to 99.9% and more preferably from 80 to 98% of individual crystals. The use of the term "individual" is understood to mean the notion of units, in contrast to an agglomerate, an aggregate or a compact mass of crystals.

Within the meaning of the invention, "crystals" is understood to mean polyhedra having a periodic structure which are directly obtained by crystallization, namely by the passage of a substance from the liquid, solvated (dissolved in a solvent) or gas state to the solid state.

Thus, a mannitol powder obtained by granulation of a crystalline composition does not constitute a powder formed of mannitol crystals within the meaning of the invention, in that the crystals of this powder are agglomerated. A person skilled in the art refers to agglomerates of crystals. Likewise, a powder obtained by atomization of a mannitol syrup does not constitute a composition formed of mannitol crystals within the meaning of the invention as this powder is composed of spheres having a spongy structure composed of microcrystals combined in a mass, with or without an amorphous phase, each sphere being obtained by the drying of a drop of the syrup sprayed during atomization. A person skilled in the art refers to atomisate. Finally, a composition formed of crystals according to the invention is distinguished from the compact masses obtained by melting in that the particles obtained are formed of microcrystals massed against one another. These compositions (agglomeratregates, atomisate and compact masses) are structurally different from the composition according to the invention and, in fact, have different physical characteristics and different applications.

According to a first alternative form, the crystallization is carried out by processes for cooling or evaporating a polyol solution.

According to a second alternative form, the crystallization is carried out by physicochemical processes. Typically, the crystallization is carried out by addition of a diluent, more particularly of an organic solvent, such as an alcohol.

According to a third alternative form, the crystallization is carried out fractionally, that is to say by successive crystallizations; the crystals obtained in each step are dissolved in a solvent and then crystallized again.

Typically, the crystallization step is followed by a step of selection of the particles, optionally preceded by a grinding of the crystals obtained.

Preferably, the selection of particles is carried out by a process of classification by sieving or on an air separator.

The particle size distribution values are determined on a type LS 230 laser diffraction particle size analyzer from Beckman-Coulter, equipped with its module for powder dispersion by aspiration (1400-watt aspirator) of the sample (dry route), following the technical manual and the manufacturer's specifications.

The operating conditions of subhopper screw speed and of intensity of vibration of the dispersion chute are determined so that the optical concentration is between 4% and 12%, ideally 8%.

The measurement range of the type LS 230 laser diffraction particle size analyzer is from 0.4 µm to 2000 µm. Results are calculated as percentage by volume and expressed in microns (µm). The calculation method used is that according to the Fraunhofer theory. Thus, a particle size of greater than 75 µm corresponds to particles measured between 75 and 2000 µm and a particle size of greater than 250 µm corresponds to particles measured between 250 and 2000 µm.

The particle size distribution curve makes it possible to additionally determine the value of the mean volume diameter (arithmetic mean) D4,3.

According to an alternative form of the invention, the pulverulent composition formed of mannitol crystals comprises a flow grade of greater than or equal to 55, preferably situated between 60 and 90, more preferably situated between 65 and 85 and more particularly still situated between 68 and 80.

The ability to flow is evaluated using the Powder Tester device of PTE type, sold by Hosokawa. This device makes it possible to measure, under standardized and reproducible conditions, the ability to flow of a powder and to calculate a flow grade, also known as flowability index, on the basis of the studies by Mr Ralph Carr (1965). The flow grade is calculated from the values obtained by the use of the following four tests: compressibility, angle of repose, angle of spatula and uniformity (see technical manual of the Powder Tester device of PTE type). For this last test, the particle size used is that obtained by laser particle size analysis described above.

Such a flow value confers, on the pulverulent composition according to the invention, good characteristics for use during the process for producing chewing gum, in particular during which precise regulation of the amount of powder to be deposited on the base gum is possible. This flow is also an advantage for many uses of the mannitol in the pharmaceutical field. It makes possible easier filling of sachets or hard gelatin capsules and also facilitates the production of tablets, allowing easier filling of the matrices of tableting presses.

According to an advantageous alternative form, the pulverulent composition formed of mannitol crystals exhibits a mannitol richness of from 96 to 100% by weight, preferably between 97 and 99.9% by weight, more preferably between 98 and 99.8% by weight.

According to another advantageous alternative form, the powder formed of mannitol crystals exhibits a compressibility of between 30 and 15%, preferably between 27 and 12% and more preferably between 24 and 10%.

Such a compressibility value confers, on the mannitol powder, better stability of its pulverulent state on storage. When the compressibility value is greater than 20%, the powder does not exhibit free flow and has a tendency to form arches in the hopper (Hosokawa PTE device handbook). For specific values of compressibility of 40-50%, it even becomes impossible to discharge the material from the hopper once the material has been stored therein.

Advantageously, the pulverulent composition formed of mannitol crystals exhibits an aerated density of greater than 0.480 g/ml, preferably of between 0.540 and 0.700 g/ml, more preferably between 0.580 and 0.650 g/ml, and a packed density of between 0.700 and 0.860 g/ml, preferably of between 0.725 and 0.830 g/ml and more preferably of between 0.750 and 0.800 g/ml.

Such an aerated density and packed density value confers, on the mannitol powder, a density sufficiently high for the packaging and transportation costs to meet commercial standards, that is to say that for manufacturers not to be obliged to package and transport a lot of air in addition to the product. On the other hand, powders with an excessively high density exhibit failings during the technological uses thereof, lack of compressibility, slow dissolution, difficulty in accurately metering.

The packed and aerated density values and the compressibility values of the pulverulent composition formed of mannitol crystals according to the invention are determined by using the Powder Tester device, type PTE, sold by Hosokawa, the manufacturer's specifications being followed.

This device makes it possible to measure, under standardized and reproducible conditions, the ability to flow of a powder by measuring in particular the bulk aerated density and the bulk packed density and to subsequently calculate, from this data, the compressibility values by the following formula:

$$\text{Compressibility} (\%) = \frac{(\text{packed density} - \text{aerated density})}{\text{packed density}} \times 100$$

The packed density and aerated density measurements are carried out on the Powder Tester device of PTE type, as mentioned above, according to the method recommended in the operating instructions for said Powder Tester (default setting 180 shaking actions for the measurement of the packed density).

Such pulverulent compositions have a particularly high resistance to caking and have very good flow and density characteristics with respect to the mannitols of the state of the art and are particularly suitable for use in processes for the manufacture of chewing gums, due to their good flow and their low tendency to create dust.

The invention also relates to the process for producing a pulverulent composition formed of mannitol crystals comprising from 72 to 99.9%, preferably from 75 to 99%, more preferably from 80 to 98% and more preferably still from 85 to 97% of particles with a particle size of greater than 75 μm according to the invention, comprising:
a) a step of crystallization of mannitol from a solvent, preferably from water,
b) a step of separation of the crystals from the suspension of crystals which is obtained,
c) a step of drying the crystals,
d) a step of selection of the crystals, and
e) a step of recovery of the pulverulent composition.

Drying can be carried out by means known to a person skilled in the art, such as fluidized air beds, for example, or an air or rotary dryer.

Separation of the crystals from the suspension of crystals obtained is typically to be carried out by a centrifuging or filtration step, the use of such centrifuging or filtration methods being known to a person skilled in the art.

Advantageously, the step d) of selection is carried out by a process of classification by sieving or using air.

"Air classifiers" are understood to mean devices which separate powders according to their particle size with the use of an air stream. Such classifiers are described in the article "Classification pneumatique" [Air classification] by Pierre Blazy and El-Aïd Jdid, Technique de l'ingénieur, traité Génie des Procédés [Techniques for the Engineer, Process Engineering Treatise]. These classifiers can have static selection chambers using a horizontal or vertical or mixed gas stream; such classifiers may or may not have baffles. Another type of air classifier is the classifier using centrifugal force. A description of the latter devices includes static cyclones, rotary classifiers comprising a horizontal axis and mechanical classifiers comprising a vertical axis.

Preferably, the crystalline powders are obtained by crystallization and then selection of particles. Preferably, the selection of particles is carried out by an air classifier. Advantageously, the air classifier is a static classifier, preferably comprising a vertical gas stream. Particularly advantageously, the air classifier is a zigzag classifier.

Such a classifier is described in U.S. Pat. No. 1,861,248.

The selection in a zigzag classifier is an air gravity selection. It is a selection process in which the solid particles are classified according to the behavior thereof during the fall thereof as, in the selection region, they are subjected to the gravitational force and to the drag force of the air flow. The selection is in fact based on the difference in trajectories of nonidentical particles in the selection region.

Advantageously, the zigzag classifier comprises several stages, the classifier preferably comprising 13 stages. The presence of these stages makes it possible to use the same air for all the stages and to repeat the selection both in the ascending stream of the light particles and in the descending air stream of the large particles.

According to a preferred embodiment of the process in accordance with the invention, the step d) of selection of the particles is carried out by a zigzag classifier comprising just one channel. Preferably, the channel exhibits a width of 20 mm and a depth of 220 mm.

The classifier is constructed by assembling a number of sections together with a fixed angle in order to create the zigzag channel. Preferably, the zigzag classifier exhibits angles of 120°. The channel has a rectangular cross section. Its specific geometry and the direction of the air flow then induce two separate streams of particles: a stream of fine particles carried away by the ascending air stream; a stream of large particles descending along the lowest wall of each section.

At each stage, the particles of the two streams are thus subjected to a new selection, after which the particles continue their movements in the stream of original particles or are transported in the stream having an opposite direction.

The performance of the classifier is determined by the behavior of the particles at each stage, on the one hand, and by the interaction between the stages, on the other hand.

The advantage of the process according to the invention is that the zigzag classifier as described makes it possible to classify a pulverulent composition formed of mannitol crystals into two fractions (fine and large).

To do this, an ascending air jet (primary air) is sent into the zigzag classifier, its speed making it possible to characterize the cutoff diameter.

The particles with a diameter greater than the cutoff diameter descend despite the air jet, whereas the others are entrained by the ascending air.

Advantageously, each stage of the zigzag classifier exhibits a height of 92 mm. Preferably, feeding is carried out at the level of the 9th stage.

According to a preferred alternative form, the step d) of selection comprises the following steps:

d.1) feeding a zigzag classifier with a pulverulent composition formed of mannitol crystals exhibiting a mean arithmetic diameter of between 80 and 145 µm, d.2) regulating the primary air flow rate so as to recover a fraction of pulverulent composition formed of mannitol crystals exhibiting an arithmetic diameter of between 100 and 300 µm, preferably from 120 to 270 µm, more preferably from 150 to 250 µm and more preferably still from 170 to 230 µm, and a particle size distribution by volume, determined by laser particle size analysis, of from 0.1 to 60%, preferably from 1 to 55%, more preferably from 1 to 40% and more preferably still from 1 to 35% of particles of greater than 250 µm.

Advantageously, the flow rate for feeding the zigzag classifier with pulverulent composition formed of mannitol crystals according to step d.1) is from 9 to 15 kg/h, preferably from 10 to 13 kg/h and more preferably 12 kg/h.

The pulverulent composition formed of mannitol crystals in accordance with the invention can advantageously be used in the food industry, for example in the fields of confectionary, more particularly in that of chewing gum.

In the field of chewing gum, as will be exemplified below, the virtual absence of fine particles in the pulverulent composition formed of mannitol crystals in accordance with the invention then makes it possible to obtain a better flowability of the powder, allowing complete replacement of the talc in the dusting of the strip of chewing gum, eliminating any problem of potential toxicity of the talc by possible contamination by asbestos, reducing the passage of the powder into the air, thereby diminishing the loss of powder, and improving the working conditions of the handlers.

However, there is nothing to prevent it from being used for any other purpose, such as, for example, in the fields:

- of baking (in the decoration of cakes, such as donuts, more particularly by its ability to flow, in metering and mixing systems in mix applications for bread- and cakemaking, industrial breadmaking (ease of metering) or industrial cakemaking,
- fondants,
- pharmaceutical forms, such as sachets, hard gelatin capsules and tablets,
- instant preparations,
- carriers for flavors,
- carriers for powerful sweeteners,
- cereals and breakfast cereals (in icing), and
- sauces free from added sugar, The invention will be even better understood using the following examples, which are not meant to be limiting and which only report certain embodiments and certain advantageous properties of the pulverulent composition formed of mannitol crystals according to the invention.

EXAMPLE 1

A mannitol syrup comprising 96% mannitol was crystallized according to European patent EP 0 202 168. Crystallization is followed by a drying step, such a powder being sold by the Applicant Company under the name Mannitol P 60.

The crystalline mannitol powder obtained is introduced into the feed hopper of a zigzag classifier, the channel of which has angles of 120°, a width of 20 mm and a depth of 220 mm. It possesses thirteen stages which each have a height of 92 mm. Feeding is carried out at the level of the 9th stage. Selection is carried out in various ways in order to obtain crystalline mannitol powders having a low fine-particle content (large fractions).

For this, the primary air feed flow rate is adjusted in particular.

This is because the speed of the ascending air defines the cutoff diameter of the starting mixture.

Thus it is that, starting from the same powder formed of mannitol crystals, in this case Mannitol 60, the use of a primary air flow rate makes it possible to vary the particle size distribution of the mannitol powders having a low fine-particle content.

The processing conditions are presented in the following table 1.

TABLE 1

| Mannitol powder according to the invention | Powder flow rate (kg/h) | Primary air flow rate (m³/h) | Flow rate of fines fraction | Flow rate of large fraction | Feed Mean arithmetic diameter (µm) D (4, 3) | Feed % by volume > 75 µm | Feed % by volume > 250 µm | Large fraction (µm) Mean arithmetic diameter (µm) D (4, 3) | Large fraction % by volume > 75 µm | Large fraction % by volume > 250 µm |
|---|---|---|---|---|---|---|---|---|---|---|
| | | | (kg/h) | (kg/h) | | | | | | |
| Product "A" | 12 | 27 | 4.2 | 7.8 | 134 | 66.5 | 10.5 | 178 | 85.7 | 18.4 |
| Product "B" | 12 | 36 | 9.6 | 2.4 | 134 | 66.5 | 10.5 | 228 | 95.1 | 32.5 |

EXAMPLE 2

The powders of example 1 were compared with the powders formed of crystalline mannitol sold by the Applicant Company under the names Mannitol 35 and Mannitol 60 and with a mannitol powder crystallized from an extract of mannitol from algae (mannitol sold under the name Brightmoon® crystalline mannitol). The results of these measurements are presented in table 2.

The powders of example 1 were compared with two samples of crystalline mannitol Mannitol 35 and Mannitol 60 (sold by the Applicant Company) and with a mannitol powder crystallized from an extract of mannitol from algae (mannitol sold under the name Brightmoon® crystalline mannitol). The results of these measurements are presented in table 2.

It is noticed, among the samples tested, that only samples A and B comprise both a flow grade reflecting very good flow characteristics and a compressibility reflecting high stability on storage. Thus, although comprising a low proportion of particles of less than 75 µm (10.7%), the mannitol extracted from algae exhibits a mean particle size of greater than 300 µm (315 µm). Conversely, although comprising a mean particle size of between 100 and 300 µm, Mannitol 60 exhibits a high content of particles of less than 75 µm of 33.5%.

These two samples exhibit a markedly lower flow than samples A and B (the mannitol extracted from algae 52%, Mannitol 60 51.5%, A 62% and B 64.5%) but nevertheless a better flow than the sample Mannitol 35 (41.5%). This demonstrates that a particle size of between 100 and 300 µm is an insufficient characteristic per se to obtain a crystalline mannitol powder having good flow. It is the same for a simple reduction in the proportion of particles of less than 75 µm. On the other hand, a high proportion of particles having a particle size of less than 75 µm and a mean particle size outside the limits 100 and 300 µm brings about very poor flow of the powder (Mannitol 35, flow rate 41.5%).

As regards the characteristic of compressibility, the mannitol extracted from algae exhibits a better stability on storage than Mannitol 60 (respectively a compressibility of 28.1 and 34.8) but these remain mediocre in comparison with samples A and B (25.2 and 19.6). Thus, the stability on storage depends both on the mean particle size of the powder and on the richness in particles of less than 75 µm. Mannitol 35, which exhibits both a high richness in particles of less than 75 µm and a mean diameter of less than 100 µm, has for its part a very high instability on storage (compressibility 43.4).

It is thus noticed that the effects brought about by these two characteristics of the crystalline mannitol powder (mean diameter of the crystalline powder and content of particles of less than 75 µm) are not additive but in fact interactive.

TABLE 2

| | Sample | | | | |
|---|---|---|---|---|---|
| | Mannitol 35 | Mannitol 60 | Product "A" | Product "B" | Mannitol extracted from algae |
| Content of particles of less than 75 µm (%) | 65.9 | 33.5 | 14.3 | 4.9 | 10.7 |
| Content of particles of greater than 250 µm | 0.01 | 10.6 | 18.4 | 32.7 | 46.1 |
| Mean diameter (µm) | 67 | 135 | 178 | 228 | 315 |
| Flow grade (out of 100) | 41.5 | 51.5 | 62 | 64.5 | 52 |
| Aerated density | 0.450 | 0.535 | 0.595 | 0.615 | 0.615 |
| Packed density | 0.795 | 0.82 | 0.795 | 0.765 | 0.855 |
| Compressibility | 43.4 | 34.8 | 25.2 | 19.6 | 28.1 |

EXAMPLE 3

A caking test is carried out in the laboratory. This test makes it possible to simulate the caking which appears in big bags (bags containing from 500 to 1500 kg of powder) of mannitol.

An amount of 1300 grams of product is placed in a polyethylene sachet, the polyethylene having a thickness of 100 µm (flat size of 32.4 cm by 20.9 cm). This sachet is subsequently hermetically closed after having driven off as much as possible of occluded air. It is subsequently placed in a perforated cylinder, with a height of 22 cm and a diameter of 13 cm, pierced with holes with a diameter 8 mm, which holes are positioned in staggered rows with a distance of 12 mm between the centers of the neighboring holes. A metal disk with a diameter just less than that of the cylinder is placed on the sachet. A weight of 6.6 kg is placed on this disk, this weight being equivalent to a pressure of 580 kg/m² identical to that which the powder situated at the bottom of a big bag is subjected to.

The setup is subsequently placed in a climate-controlled chamber regulated so as to subject it to 15 cycles of 6 hours (3 hours at a temperature of 15° C. and a relative humidity of 85% and then 3 hours at a temperature of 30° C. and a relative humidity of 85%).

At the end of these cycles, the sachet is carefully removed from the cylinder and cut open. A first observation of the powder is carried out. All the powder is subsequently introduced into a 5 liter can (diameter of the opening greater than the diameter of the perforated cylinder), which is rotated for one minute in a Mixomat A14 (Fuchs/Switzerland) tumbler mixer. All of the powder is subsequently poured onto a sieve, the meshes of which have square openings of approximately 8 mm by 8 mm. Thus, only the lumps of product with a diameter of greater than approximately 8 mm are recovered, the total weight of which is measured. The content of caked product is calculated by dividing the weight of these lumps by the starting weight of mannitol employed (1300 grams).

TABLE 3

| | Sample | | | | |
|---|---|---|---|---|---|
| | Mannitol 35 | Mannitol 60 | A | B | Mannitol extracted from algae |
| Appearance of the powder | Hard block | Crumbly block | Very crumbly block | Fluid powder | Very crumbly block |
| Content of caked product | 24% | 18% | 8% | 0% | 10% |

Mannitol 35 and Mannitol 60 have a high content of caked product, which indicates that the powder situated at the bottom of the big bags will very rapidly acquire cohesion after filling and that these big bags will become very difficult to empty. This packaging is thus inadvisable for these two samples. For sample A and the mannitol extracted from algae, which exhibit a degree of caking at 8%-10%, this packaging can thus be envisaged but storage will have to be limited in time. For sample B, the filling, the storing and the emptying of the big bags will not present any difficulty: it can thus be sold without concern in this type of device.

EXAMPLE 4

Chewing gum is produced industrially on a Togum (Bosch-Togum) brand production line.

This operation is carried out with a standard "sugar-free" chewing gum formulation:
 Base gum: 32%
 Sorbitol powder, Neosorb® P60W: 49%
 Mannitol 60: 7%
 Maltitol syrup, Lycasin® 80/55HDS: 9%
 Glycerin: 0.2%
 Aspartame: 0.2%
 Mint flavoring, liquid: 2.1%
 Mint flavoring, powder: 0.5%

The mixing stage is carried out in a Togum GT120 Z-arm kneading machine, with a capacity of approximately 60 kg. The mixing is carried out continuously.

At t=0, the base gum, preheated overnight at 50° C., and half the sorbitol powder are introduced into the kneading machine. At t=3 min, the mannitol is introduced, at t=5 min, the maltitol syrup is introduced, at t=7 min, half of the sorbitol and the aspartame are introduced, at t=11 min, the glycerin is introduced and, at t=12 min, the flavorings are introduced. At t=16 min, mixing is halted and the paste is discharged. The temperature of the paste is then approximately 55° C. The paste is divided into bars of approximately 2 kg which are stored at 20° C. and 50% relative humidity for 1 hour, which will bring the temperature of the paste to 47° C. before extrusion.

The extrusion step is carried out on a Togum TO-E82 device, with the body of the extruder heated to 40° C. and the head to 45° C.

The dusting step and the rolling step are carried out on a Togum TO-W191 rolling mill. It is equipped firstly with two dusting stations, one located over the top of the extruded strip of chewing gum and one above a conveyor belt situated below the strip of chewing gum, the role of which is to contribute the dusting powder over the internal face of the chewing gum. Thus, the strip of chewing gum is dusted over both faces before the first rolling station. It is subsequently equipped with four pairs of rolling rollers with, located between the second and third pairs, a dust-removing system consisting of a pair of brushes, one located over the bottom and the other over the top of the strip of chewing gum. This system serves to remove the excess powder on both faces of the strip of chewing gum. Finally, it is equipped with two pairs of rollers for the forming and the cutting, in order to confer the desired final form on the chewing gum, in the present case cushions.

The mannitol powders of example 2 were tested in dusting. The dusting powder consisted solely of these mannitol powders: no talc was added.

The observations made were: the ease of obtaining flow of the powder from the dusting equipment, the control of the amount of powder deposited with respect to the desired amount, the amount of powder lost, the formation of dust in suspension in the air, and the appearance of the chewing gum after the removal of dust. Furthermore, the chewing gums were tested by a panel of 15 people in order to determine if the increase in the size of the particles of the dusting powder confers a gritty texture on the chewing gum. The tests are carried out according to the standard AFNOR V 09-014 (April 1982) on samples A to Z per group of 5 or 6 samples per test. The 5 or 6 samples were presented simultaneously, a different order of tasting being stipulated for each member of the panel. The descriptor stipulated, namely the gritty nature in the mouth, is evaluated on a 6-point scale graded in the following way: absence, very slight, slight, marked, pronounced, very pronounced. The analysis of variance (Friedman's ANOVA) distinguishes the samples with regard to their gritty natures ($p \ll 0.05$). The values obtained are shown in table 4.

TABLE 4

| | Sample | | | | |
|---|---|---|---|---|---|
| | Mannitol 35 | Mannitol 60 | Sample A | Sample B | Mannitol extracted from algae |
| Flow of the powder | Poor | Poor | Moderate | Good | Poor |
| Control of the amount of powder dusted | Poor | Fair | Fairly good | Good | Poor |
| Amount of powder lost | Very high | High | Moderate | Slight | Moderate |
| Particles in suspension in the air | Many | Many | Few | Very few | Very few |
| Appearance of the chewing gum after removal of dust | Conforms | Conforms | Conforms | Conforms | Conforms |
| Gritty sensation on tasting in the mouth | Absence | Absence | Absence | Absence | Marked |

Mannitol 35, Mannitol 60 and the mannitol extracted from algae exhibit poor flow, which makes it difficult to regulate the dusting equipment. The amount deposited is thus difficult to control. Consequently, the level of loss is high. In point of fact, while Mannitol 35 and Mannitol 60 comprise a content of particles of less than 75 µm of greater than 28%, the mannitol extracted from algae for its part comprises a particularly low content of these same particles. Samples A and B, which exhibit less than 25% of particles of less than 75 µm and a mean particle diameter of 178 and 228 µm, have a flow which makes it possible to control the amount of powder deposited and to limit the losses.

Furthermore, because of the presence of fines in Mannitol 35 and Mannitol 60, the level of particles in suspension in the air is high, in contrast to samples A and B or to the mannitol extracted from algae, for which a low density of particles in the air is observed. The small amount of particles in suspension is an advantage for the cleanliness of the premises and the health of the operators.

The mean diameter of the powders A and B makes it possible both to promote the flow of the powders and to reduce the level of particles in the air during the handling of these powders, while not having negative consequences with regard to the organoleptic qualities of the chewing gum obtained. Specifically, whereas the use of mannitol extracted from algae induces a gritty sensation in the mouth, samples A and B, while making possible good management of the deposition of dusting powder with a reduced level of powder in suspension in the air and also uniform dusting of the strips of chewing gum after removal of dust, do not result in any gritty sensation in the mouth.

The invention claimed is:

1. A pulverulent composition formed of mannitol crystals being of a polyhedral structure which is obtained by (i) crystallization of mannitol from a solvent, followed by (ii) a step of separation of the crystals from the suspension of crystals which is obtained, (iii) a step of drying the crystals in manner other than granulation or spray-drying and (iv) a step of selection, wherein the crystals are not constituted by agglomerates or atomisates, wherein the particle size distribution by volume, determined by laser particle size analysis, exhibits:
   from 72 to 99.9% of particles with a particle size of greater than 75 µm,
   from 0.1 to 60% of particles of greater than 250 µm,
   a mean diameter of 100 to 300 µm.

2. The pulverulent composition as claimed in claim 1, wherein the pulverulent composition has an aerated density of greater than 0.480 g/ml and a packed density of between 0.700 and 0.860 g/ml.

3. The pulverulent composition as claimed in claim 1, wherein the pulverulent composition has a flow grade of greater than or equal to 55.

4. The pulverulent composition as claimed in claim 3, wherein the pulverulent composition has a mannitol richness is from 96 to 100% by weight.

5. The pulverulent composition as claimed in claim 3, wherein the pulverulent composition has a compressibility of between 30 and 15%.

6. The pulverulent composition as claimed in claim 3, wherein the pulverulent composition has an aerated density of greater than 0.480 g/ml and a packed density of between 0.700 and 0.860 g/ml.

7. The pulverulent composition as claimed in claim 1, wherein the pulverulent composition has a mannitol richness is from 96 to 100% by weight.

8. The pulverulent composition as claimed in claim 7, wherein the pulverulent composition has a compressibility of between 30 and 15%.

9. The pulverulent composition as claimed in claim 7, wherein the pulverulent composition has an aerated density of greater than 0.480 g/ml and a packed density of between 0.700 and 0.860 g/ml.

10. The pulverulent composition as claimed in claim 1, wherein the pulverulent composition has a compressibility of between 30 and 15%.

11. The pulverulent composition as claimed in claim 10, wherein the pulverulent composition has an aerated density of greater than 0.480 g/ml and a packed density of between 0.700 and 0.860 g/ml.

12. A process for producing a pulverulent composition formed of mannitol crystals being of a polyhedral structure and comprising from 72 to 99.9% of particles with a particle size of greater than 75 said process comprising:
   a) a step of crystallization of mannitol from a solvent,
   b) a step of separation of the crystals from the suspension of crystals which is obtained,
   c) a step of drying the crystals in manner other than granulation or spray-drying,
   d) a step of selection of the crystals having a mean diameter of 100 to 300 µm, and
   e) a step of recovery of the pulverulent composition,
   wherein the crystals of the pulverulent composition are formed by the step of crystallization from the solvent, and the crystals are not constituted by agglomerates or atomisates.

13. The process as claimed in claim 12, wherein the step d) of selection is carried out by sieving or with an air classifier.

14. The process as claimed in claim 13, wherein the step d) of selection is carried out with a zigzag classifier.

15. The process as claimed in claim 14, wherein the step d) of selection comprises the following steps:
   d.1) feeding a zigzag classifier with a pulverulent composition formed of mannitol crystals exhibiting a mean arithmetic diameter of between 80 and 145 µm,
   d.2) regulating the primary air flow rate so as to recover a fraction of pulverulent composition formed of mannitol crystals exhibiting a mean diameter of from 100 to 300 µm and a particle size distribution by volume, determined by laser particle size analysis, of from 0.1 to 60% of particles of greater than 250 µm.

16. The process as claimed in claim 14, wherein the step d) of selection is carried out with a zigzag classifier comprising several stages.

17. The process as claimed in claim 9, wherein the step d) of selection of the particles is carried out by a zigzag classifier comprising just one channel, this channel exhibiting a width of 20 mm and a depth of 220 mm.

18. The process as claimed in claim 16, wherein the step d) of selection comprises the following steps:
   d.1) feeding a zigzag classifier with a pulverulent composition formed of mannitol crystals exhibiting a mean arithmetic diameter of between 80 and 145 µm,
   d.2) regulating the primary air flow rate so as to recover a fraction of pulverulent composition formed of mannitol crystals exhibiting a mean diameter of from 100 to 300 µm and a particle size distribution by volume, determined by laser particle size analysis, of from 0.1 to 60% of particles of greater than 250 µm.

19. The process as claimed in claim 14, wherein the step d) of selection of the particles is carried out by a zigzag classifier comprising just one channel, this channel exhibiting a width of 20 mm and a depth of 220 mm.

20. The process as claimed in claim 19, wherein the step d) of selection comprises the following steps:
   d.1) feeding a zigzag classifier with a pulverulent composition formed of mannitol crystals exhibiting a mean arithmetic diameter of between 80 and 145 µm,
   d.2) regulating the primary air flow rate so as to recover a fraction of pulverulent composition formed of mannitol crystals exhibiting a mean diameter of from 100 to 300 µm and a particle size distribution by volume, determined by laser particle size analysis, of from 0.1 to 60% of particles of greater than 250 µm.

* * * * *